United States Patent [19]

Hour

[11] Patent Number: 5,326,037
[45] Date of Patent: Jul. 5, 1994

[54] AUTOMATIC WASHING AND STERILIZING DEVICE FOR A STABLE

[76] Inventor: Tyh-Yuan Hour, 82, To-Syn Village, Luh-Jeau Shian, ChiaYi Hsien, Taiwan

[21] Appl. No.: 74,748

[22] Filed: Jun. 10, 1993

[51] Int. Cl.⁵ .......................... B05B 3/14; B05B 3/18
[52] U.S. Cl. .................... 239/743; 239/752; 239/751
[58] Field of Search ........... 239/743, 750, 751, 752, 239/264; 134/172, 180, 181

[56] References Cited

U.S. PATENT DOCUMENTS

| | | | |
|---|---|---|---|
| 3,383,046 | 5/1968 | Voegtly | 239/752 |
| 3,908,907 | 9/1975 | Beltran | 239/752 |
| 3,985,161 | 10/1976 | Nelson | 239/751 |
| 4,805,648 | 2/1989 | Hour | 134/57 |
| 4,981,268 | 1/1991 | Hour | 239/752 |

FOREIGN PATENT DOCUMENTS 5492 of 1912 United Kingdom ................ 239/752

Primary Examiner—Andres Kashnikow
Assistant Examiner—Lesley D. Morris
Attorney, Agent, or Firm—Larson and Taylor

[57] ABSTRACT

An automatic washing and sterilizing device for a stable comprising a crane moving on a steel cable at various speeds and a nozzle mounted on the crane for spraying water for washing or sterilizing solution for sterilization all over in a stable.

2 Claims, 2 Drawing Sheets

AUTOMATIC WASHING AND STERILIZING DEVICE FOR A STABLE

BACKGROUND OF THE INVENTION

The present invention relates to a washing and sterilizing device, and more particularly to an automatic device for use in washing and sterilizing in a stable.

The U.S. Pat. No. 4,805,648 granted to this applicant discloses an automatic device for use in washing and sterilizing stables for farm animals. The device comprises two cranes, each of which is provided with a pipe for conveying fluids, such as water and disinfectant. The fluids can be emitted through a nozzle, which can be caused to swivel within a predetermined angular range by means of a threaded rod that can be moved up and down by a power wheel controlled by a motor capable of decelerating.

Another U.S. Pat. No. 4,981,268 granted to the applicant of the present invention discloses an improved automatic device for washing and sterilizing stables for farm animals. Such an improved device comprises a crane provided with a nozzle for emitting fluids such as water and disinfectant. The crane includes mainly a motor, a gear, a plurality of pulleys, and two winding wheels powered by the motor via the gear. The crane can be actuated to travel on a guide cable by the winding of an actuating wire which is wound on the two winding wheels. The device is further provided with a timer to control the timing of the motion of the motor.

The prior art devices described above are limited in that the emitting angle of the nozzles can not be easily altered as required and that the cranes can not be caused to travel at various speeds.

SUMMARY OF THE INVENTION

It is therefore the primary object of the present invention to provide an automatic washing and sterilizing device for a stable, which is so improved as to overcome the shortcomings of the prior art devices described previously.

In keeping with the principles of the present invention, the foregoing object of the present invention is attained by an automatic device for washing and sterilizing in a stable, which comprises mainly a crane and a nozzle. The crane is composed of two winding wheels fastened respectively to two shafts. Each of the two winding wheels is provided with a plurality of annular grooves of various widths or diameters, which enable the crane to travel at various speeds when a steel wire is wound in the annular grooves of the winding wheels. One of the two shafts is provided with a sector gear which is rotatably mounted on one end of a threaded rod having another end fastened with an eccentric rod which is in turn coupled with a linking rod enabling the nozzle to swivel freely.

DETAILED DESCRIPTION OF THE INVENTION

Figure 1:
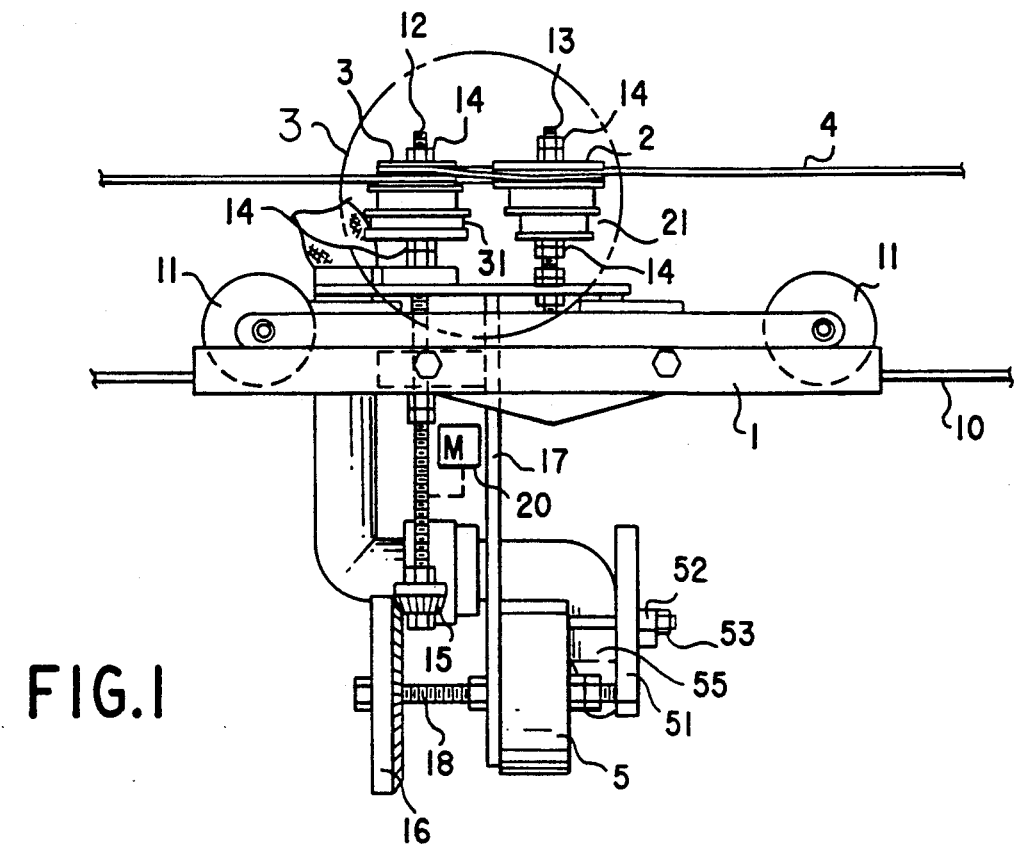
FIG. 1 shows a side elevational view of the present invention.

Referring to FIG. 1, the device of the present invention is shown to comprise a crane 1 capable of traveling on a steel cable 10 by means of two pulleys 11. The crane 1 is composed of two threaded shafts 12 and 13, on which two winding wheels 3 and 2 are respectively mounted. The winding wheels 3 and 2 can be adjustably located on the threaded shafts 12 and 13 and then fastened by means of a nut 14 engageable with the threaded shaft 12 or the threaded shaft 13. In addition, the winding wheels 2 and 3 are so mounted that they can be idled respectively.

Figure 3:
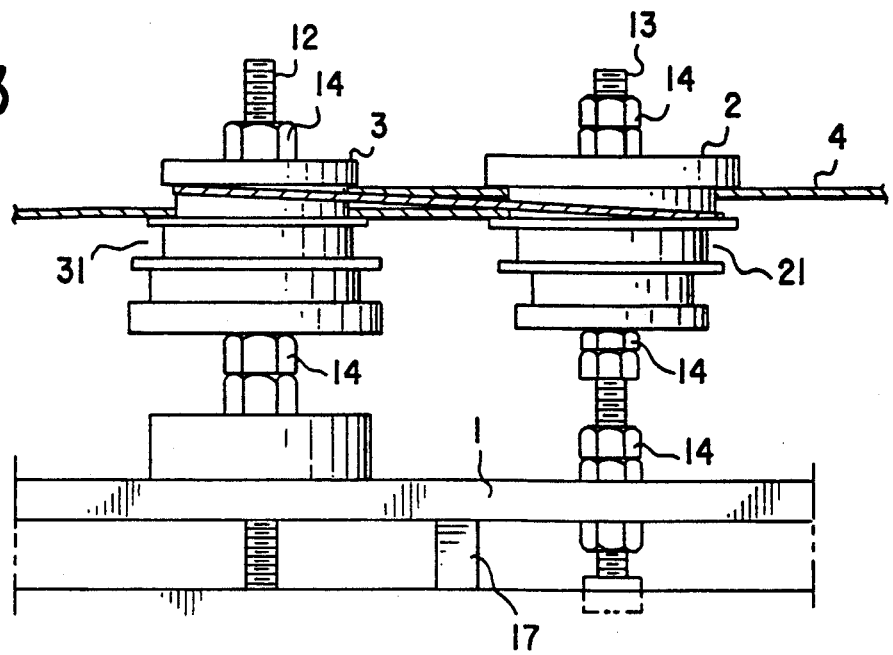
FIG. 3 shows a perspective enlarged view of a portion indicated by a circle "3" as shown in FIG. 1.
Figure 4:
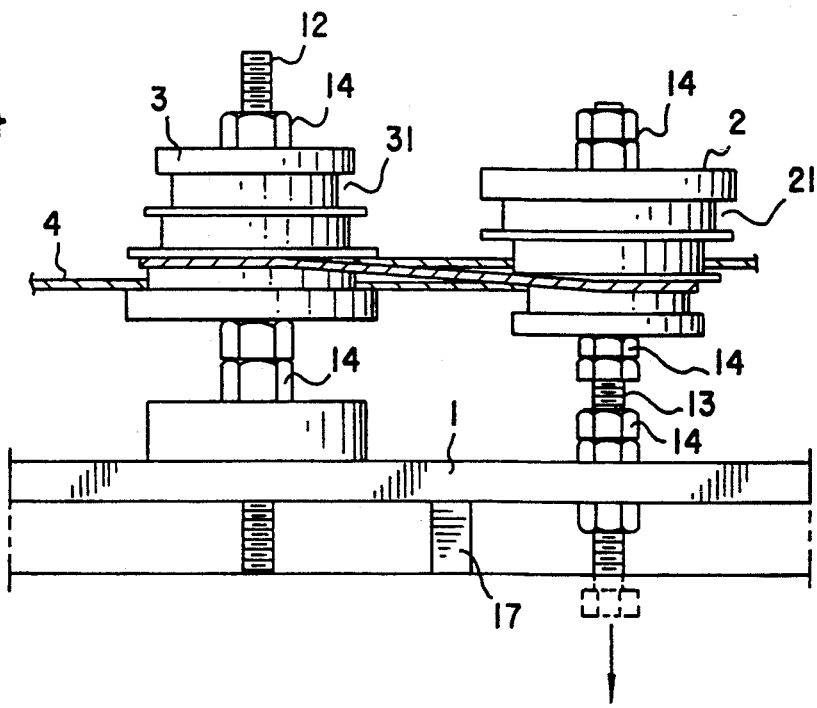
FIG. 4 shows a schematic view of the motion of the portion as shown in FIG. 3.

Now referring to FIGS. 1 and 3, the winding wheels 2 and 3 are shown to be arranged in such an opposite manner that the wider diameter portion of the winding wheel 2 faces upwards while the wider diameter portion of the winding wheel 3 faces downwards. The winding wheels 2 and 3 are provided thereon respectively and symmetrically with a plurality of grooves 21 and 31 of various diameters. The grooves each are so constructed that they are progressively of wider diameters from the bottom of the winding wheel toward the top of the winding wheel, or vice versa. The winding wheel 2 can be properly located by adjusting the nut 14, as shown in FIG. 4. The threaded shaft 12 is driven by a motor 20 (shown with a schematic connection) to rotate at a constant speed. As a result, the crane 1 may travel on the steel cable 10 at various speeds depending on which groove 31 of the winding wheel 3 is selected as having a steel wire 4 winding in it. The tension of the steel wire 4 winding on the winding wheel 3 is adjusted by the winding wheel 2 in a complementary manner and by the winding wheel 3 which can move up and down.

Figure 2:
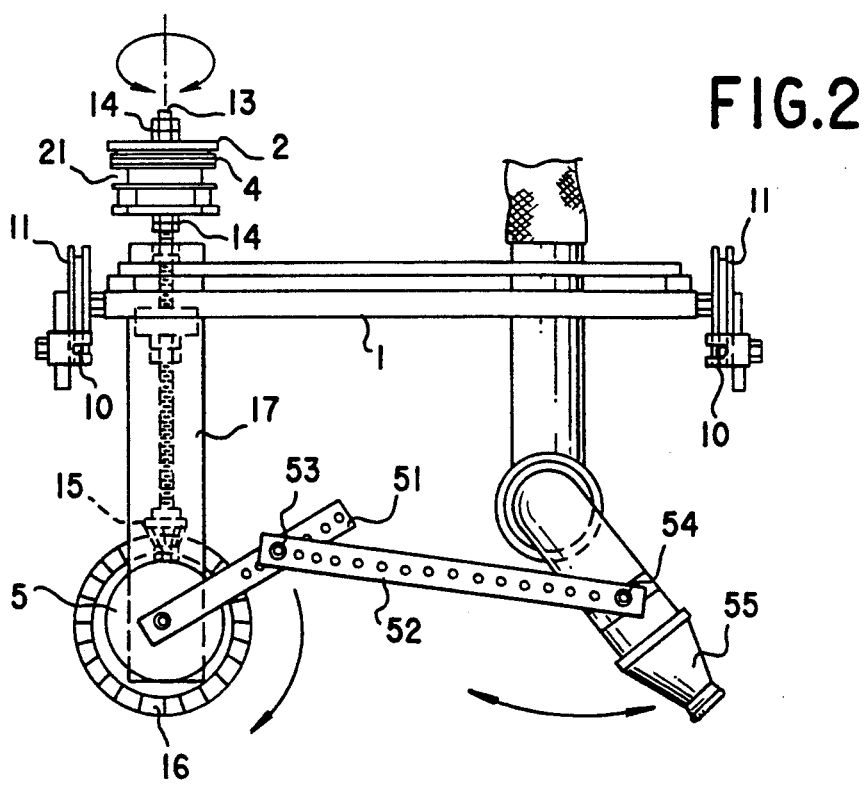
FIG. 2 shows a front elevational view of the present invention.

As shown in FIGS. 1 and 2, the threaded shaft 12 is provided at the bottom thereof with two sector gears 15 and 16 which engage each other. The sector gear 16 is rotatably mounted on a threaded rod 18 which is in turn fastened securely with a base plate 17 and is rotatably mounted on an upper base seat 5. The threaded rod 18 is coupled with an eccentric rod 51 capable of rotating synchronously along with the threaded rod 18. There is a linking rod 52 that is fastened with the eccentric rod 51 by means of a fastening element 53 which engages the fastening holes of the eccentric rod 51 and the linking rod 52. Fastened by means of a fastening element 54 at one end of the linking rod 52 is a nozzle 55. The emitting angle of the nozzle 55 can be adjusted freely by changing the way that the nozzle 55 is fastened to the linking rod 52 by means of the fastening element 54.

The embodiment of the present invention described above is to be regarded in all respects as merely illustrative and not restrictive. Accordingly, the present invention may be embodied in other specific forms without deviating from the spirit thereof. The present invention is therefore to be limited only by the scope of the following appended claims.

What is claimed is:

1. An automatic washing and sterilizing device for a stable comprising;
 a crane mounted for movement along a steel cable;
 first and second threaded shafts which are mounted to said crane and which extend from said crane adjacent one another;
 a motor for rotating said first shaft;
 first and second winding wheels, each said winding wheel being provided with a plurality of grooves of progressively different diameters about which a tension wire is wound;

a first mounting means for mounting said first winding wheel to said first shaft for rotation therewith;

a second mounting means for mounting said second winding wheel for rotation on said second shaft;

at least one of said mounting means allowing its associated one of said winding wheels to be adjustably positioned on its associated one of said shafts such that a selected one of said grooves of the one of said winding wheels engages the tension wire while an adjacent selected one of said grooves of the other of said winding wheels also engages the tension wire; and a nozzle fastened to said crane for movement therewith.

2. An automatic washing and sterilizing device as claimed in claim 1 and further including a first sector gear attached to said first shaft for rotation therewith, a third threaded shaft extending adjacent said first sector gear and having a second sector gear mounted thereto which engages said first sector gear and rotates said third shaft when said first shaft rotates, a first rod mounted to said third shaft for rotation of a distal portion thereof about said third shaft, a second rod having one end portion pivotally and adjustably attached to said nozzle and the other end portion pivotally and adjustably attached to said distal portion of said first rod, and a means for mounting said nozzle for pivotal movement relative to said crane such that when said distal portion of said first rod is rotated with said first threaded shaft said second rod is moved which causes said nozzle to pivot.

* * * * *